United States Patent
Iishi et al.

(10) Patent No.: US 7,297,790 B2
(45) Date of Patent: Nov. 20, 2007

(54) ANHYDROUS MIRTAZAPINE CRYSTALS AND PROCESS FOR PREPARING THE SAME

(75) Inventors: Eiichi Iishi, Osaka (JP); Yoshiyuki Imamiya, Osaka (JP)

(73) Assignee: Sumitomo Chemical Company, Limited, Osaka-shi (JP)

( * ) Notice: Subject to any disclaimer, the term of this patent is extended or adjusted under 35 U.S.C. 154(b) by 0 days.

(21) Appl. No.: 10/743,740

(22) Filed: Dec. 24, 2003

(65) Prior Publication Data

US 2004/0138447 A1 Jul. 15, 2004

Related U.S. Application Data

(60) Division of application No. 10/337,277, filed on Jan. 7, 2003, now Pat. No. 6,723,845, which is a division of application No. 10/041,495, filed on Jan. 10, 2002, now Pat. No. 6,552,189, which is a division of application No. 09/697,329, filed on Oct. 27, 2000, now abandoned, which is a continuation-in-part of application No. PCT/JP00/04835, filed on Jul. 19, 2000.

(30) Foreign Application Priority Data

Nov. 24, 1999 (JP) .................................. 11-333049
Mar. 10, 2000 (JP) ................................. 2000-67476

(51) Int. Cl.
C07D 471/14 (2006.01)
(52) U.S. Cl. ..................................................... 540/578
(58) Field of Classification Search ................ 540/578
See application file for complete search history.

(56) References Cited

U.S. PATENT DOCUMENTS

| | | | |
|---|---|---|---|
| 4,062,848 A | 12/1977 | van der Burg | |
| 4,524,146 A | 6/1985 | Yokoyama | |
| 5,284,857 A | 2/1994 | Press et al. | |
| 5,397,790 A | 3/1995 | Butera et al. | |
| 5,401,753 A | 3/1995 | Butera et al. | |
| 5,468,768 A | 11/1995 | Cipollina et al. | |
| 5,583,149 A | 12/1996 | Cipollina et al. | |
| 6,552,189 B2 | 4/2003 | Iishi et al. | |
| 2001/0051718 A1 | 12/2001 | Singer et al. | |
| 2002/0065413 A1 | 5/2002 | Maeda et al. | |
| 2002/0072602 A1 | 6/2002 | Singer | |

FOREIGN PATENT DOCUMENTS

JP 07-247286 9/1995
WO WO 00/62782 A1 10/2000

OTHER PUBLICATIONS

Kaspersen et al. {Journal of Label. comp. and Radiopharm., 27, No. 9, 1055 (1989)}.*

Kaspersen et al. "The synthesis of org 3770 Labelled with 3H, 13C and 14C," Journal of Label. Comp. and Radiopharm., vol. 27, No. 9, pp. 1055 (1989).

H. Tomori et al., Bull. Chem. Soc. Jpn., vol. 69, No. 12, pp. 3581-3590, 1996.

Marjo Merslavic, Ph.D., "The Synthesis of Mirtazapine", Affidavit of Mr. Merslavic, Jul. 28, 2004.

Extract from Hunnius, Pharmazeutisches Wörterbuch, 8$^{th}$ Edition, de Gruyter 1998, p. 682.

Additional Experiment of EXAMPLE 1, process 4 of US Patent No. 4,062,848 (van der Burg), which was filed on Sep. 29, 2005 with the European Patent Office during the prosecution of the Opposition in the corresponding European Patent.

Notice of Opposition dated May 9, 2007 with Letter from Opponent and Documents P22 (Experimental Report) and P23 ( Examination Procedure document) attached thereto.

L.M. Harwood et al., Experimental Organic Chemistry, Blackwell Scientific Publications, 1989, pp. 136-137.

* cited by examiner

Primary Examiner—Kahsay Habte
(74) Attorney, Agent, or Firm—Birch, Stewart, Kolasch & Birch, LLP

(57) ABSTRACT

Low-hygroscopic anhydrous mirtazapine crystals having a hygroscopic degree of not more than 0.6% by weight when the crystals are stored in the air having a relative humidity of 75% at 25° C. under atmospheric pressure for 500 hours; a process for preparing anhydrous mirtazapine crystals having a hygroscopic degree of not more than 0.6% by weight when the crystals are stored in the air having a relative humidity of 75% at 25° C. under atmospheric pressure for 500 hours, comprising drying crystals of mirtazapine hydrate; a crystal of a mirtazapine hydrate represented by the formula (I):

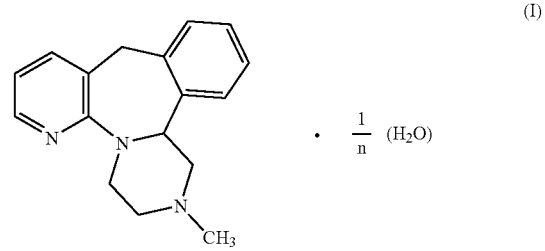

(I)

wherein n is an integer of 1 to 5; and a process for preparing crystals of a mirtazapine hydrate, comprising crystallizing a crude mirtazapine using a water-soluble organic solvent and water. The anhydrous mirtazapine crystals can be suitably used, for instance, as an antidepressant.

6 Claims, 9 Drawing Sheets

ANHYDROUS MIRTAZAPINE CRYSTALS AND PROCESS FOR PREPARING THE SAME

This application is a divisional application of application Ser. No. 10/337,277, filed on Jan. 7, 2003 now U.S. Pat. No. 6,723,845 which is a divisional application of application Ser. No. 10/041,495, filed on Jan. 10, 2002 (now U.S. Pat. No. 6,552,189) which is a divisional application of application Ser. No. 09/697,329, filed on Oct. 27, 2000, now abandoned and for which priority is claimed under 35 U.S.C. § 120. Application Ser. No. 09/697,329 is a continuation-in-part of PCT International Application No. PCT/JP00/04835 filed on Jul. 19, 2000 under 35 U.S.C. § 371. This application also claims priority of Application Nos. 11-333049 and 2000-67476, both filed in Japan on Nov. 24, 1999 and Mar. 10, 2000, respectively, under 35 U.S.C. § 119. The entire contents of each of the above-identified applications are hereby incorporated by reference.

BACKGROUND OF THE INVENTION

1. Field of the Invention

The present invention relates to anhydrous mirtazapine crystals and a process for preparing the same, and crystals of a mirtazapine hydrate and a process for preparing the same. More specifically, the present invention relates to anhydrous mirtazapine crystals having low hygroscopic properties, which are useful as an antidepressant, and a process for preparing the same, and crystals of a mirtazapine hydrate, which are useful as a preparation intermediate for the anhydrous mirtazapine crystals, and a process for preparing the same.

2. Discussion of the Related Art

As a process for increasing the purity of mirtazapine, there has been proposed a process for recrystallizing mirtazapine from a petroleum ether or the like (U.S. Pat. No. 4,062,848).

However, there are some defects in this process that impurities are precipitated in an oily state when a crude mirtazapine having a purity of 95 to 99% or so is used, so that the crystallization of mirtazapine is inhibited, and that it would be difficult to crystallize mirtazapine having a high purity.

In addition, since the crystals of mirtazapine have hygroscopic properties, there are some defects in the crystals that they cannot be handled and stored if they are not under dry conditions.

Accordingly, there have been earnestly desired the development of a process capable of efficiently preparing, mirtazapine having a high purity from a crude mirtazapine, and the development of mirtazapine crystals having low hygroscopic properties.

The present invention has been accomplished in view of the prior art described above. An object of the present invention is to provide a process capable of efficiently preparing a high-purity mirtazapine from a crude mirtazapine, and anhydrous mirtazapine crystals having, low hygroscopic properties and a process for preparing the same; and crystals of a mirtazapine hydrate, which are useful as a preparation intermediate for the anhydrous mirtazapine crystals and a process for preparing the same. These and other objects of the present invention will be apparent from the following description.

SUMMARY OF THE INVENTION

According, to the present invention, there are provided:
(1) low-hygroscopic anhydrous mirtazapine crystals having a hygroscopic degree of not more than 0.6% by weight when the crystals are stored in the air having a relative humidity of 75% at 25° C. under atmospheric pressure for 500 hours;
(2) a process for preparing low-hygroscopic anhydrous mirtazapine crystals having a hygroscopic degree of not more than 0.6% by weight when die crystals are stored in the air having, a relative humidity of 75% at 25° C. under atmospheric pressure for 500 hours, comprising, drying crystals of mirtazapine hydrate; and
(3) a crystal of a mirtazapine hydrate represented by the formula (I):

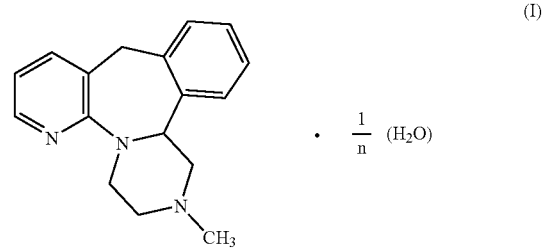

wherein n is an integer of 1 to 5, and a process for preparing the same.

DETAILED DESCRIPTION OF THE INVENTION

Figure 1:
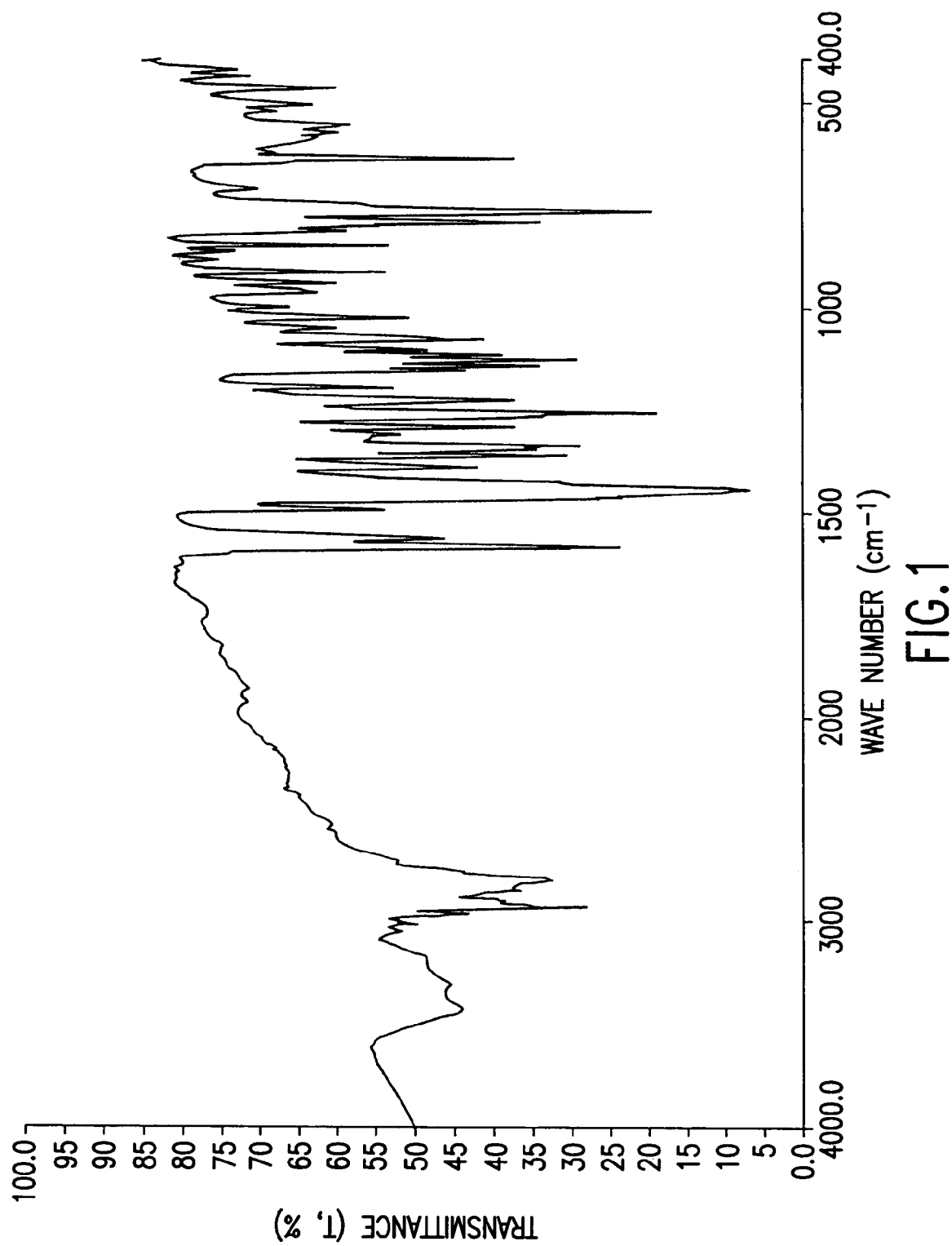
FIG. 1 is a chart showing infrared absorption spectrum of the crystals of the mirtazapine hydrate obtained in Example 1 of the present invention.

In the present specification, the term "anhydrous" of the anhydrous mirtazapine crystals means that the mirtazapine crystals do not substantially contain moisture. More specifically, it is desired that the water content of the anhydrous mirtazapine crystals is not more than 0.5% by weight, preferably not more than 0.3% by weight, from the viewpoint of imparting sufficient low hygroscopic properties to the crystals.

The low-hygroscopic anhydrous mirtazapine crystals of the present invention have a hygroscopic degree of not more than 0.6% by weight when the crystals are stored in the air having a relative humidity of 75% at 25° C. under atmospheric pressure for 500 hours. Therefore, the handling of the crystals and its formation into preparations are facilitated, and the storage stability is improved.

As a starting material of the anhydrous mirtazapine crystals, crystals of a mirtazapine hydrate can be used.

As the crystal of a mirtazapine hydrate, there can be cited a compound represented by the formula (I):

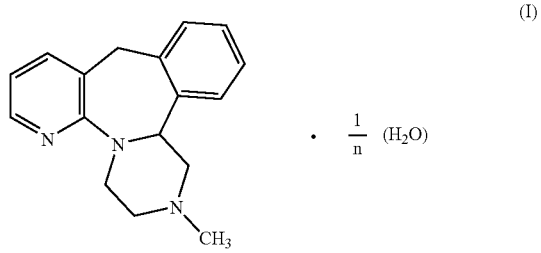

wherein n is an integer of 1 to 5. In the formula, it is preferable that n is 2 or 3. Among them, it is preferable that n is 2, i.e. a crystal of mirtazapine hemihydrate, from the viewpoints of crystallinity, handling and storage stability. The crystal of the mirtazapine hemihydrate has characteristic diffraction peaks in the X-ray diffraction pattern, when angles of diffraction (2θ) are 9.28, 14.36, 20.46 and 26.92.

The crystals of a mirtazapine hydrate can be readily prepared from, for instance, a crude mirtazapine as a starting material by the following method. The crude mirtazapine is one having a purity of not more than 99% or so, and can be prepared, for instance, by a process disclosed in U.S. Pat. No. 4,062,848.

More specifically, the crude mirtazapine used in the present invention refers to one having an absorbance of not less than 0.1 at a wavelength of 600 nm and a transmittance of not more than 30% at a wavelength of 400 nm, when the absorbance at a wavelength of 600 nm and the transmittance at a wavelength of 400 nm are determined using a 10 mm quartz cell in which 2 g of a crude mirtazapine dissolved in 10 mL of methanol is placed by means of a measuring device [commercially available from Shimadzu Corporation under the trade name of UV-2500PC], and also having b value shown by a colorimeter of not less than 10, when determined by using a colorimeter commercially available from Nippon Denshoku Kogyo Kabushiki Kaisha under the trade name of calorimeter Z-300A.

In the preparation of the crystals of a mirtazapine hydrate from a crude mirtazapine, firstly, the crude mirtazapine is dissolved in a solvent.

The solvent includes a mixed solvent of a water-soluble organic solvent such as lower alcohols such as methanol and ethanol; ethers such as dioxane and tetrahydrofuran; ketones such as acetone; esters such as methyl acetate; and aprotic organic solvents such as dimethylformamide and dimethyl sulfoxide, with water. Among the water-soluble organic solvents, the lower alcohols such as methanol and ethanol are preferable. It is desired that the amount of water is 50 to 2000 parts by weight, preferably 80 to 1000 parts by weight, based on 100 parts by weight of the water-soluble organic solvent, from the viewpoints of improvement in yield and improvements in purity and hue.

It is desired that the amount of the solvent is usually 50 to 3000 parts by weight, preferably 50 to 2000 parts by weight, more preferably 100 to 1000 parts by weight, based on 100 parts by weight of mirtazapine, from the viewpoints of improvement in yield and improvements in purity and hue.

The temperature at which the crude mirtazapine is dissolved in the solvent is not limited to specified ones. It is desired that the temperature is usually 0° to 80° C., preferably 0° to 60° C., more preferably 0° to 10° C., from the viewpoints of precipitating impurities as insoluble matters and efficiently removing them.

When the crude mirtazapine is dissolved in the solvent at a temperature of 60° to 80° C., it is preferable to add water to a crude mirtazapine solution obtained by dissolving the crude mirtazapine in the solvent, from the viewpoint of improving the purity of the resulting mirtazapine hydrate. It is preferable that the amount of water is 10 to 100 parts by weight or so, based on 100 parts by weight of the solvent, from the viewpoints of improvements in purity and hue.

In addition, in order to improve hue, a decolorizing carbon may be added properly to the crude mirtazapine solution. It is preferable that the amount of the decolonizing carbon used is 0.5 to 10 parts by weight or so, based on 100 parts by weight of the crude mirtazapine, from the viewpoints of improvements in purity and hue.

It is preferable that a crude mirtazapine solution to which the decolorizing carbon is added is stirred at a temperature of 0° to 70° C. or so, preferably 0° to 30° C. or so, for 10 to 60 minutes in order to improve hue.

Next, the decolorizing carbon is filtered, and the decolorizing carbon is washed with a water-soluble organic solvent such as methanol, ethanol, dioxane, tetrahydrofuran, acetone, methyl acetate, dimethylformamide, or dimethyl sulfoxide. Thereafter, in order to obtain a uniform crystal, it is preferable to cool the resulting mirtazapine solution to a temperature of 0° to 10° C.

It is preferable that water is added in a thin stream to the resulting mirtazapine solution in an amount of 100 to 1000 parts by weight or so based on 100 parts by weight of the crude mirtazapine, from the viewpoint of crystallization. Thereafter, the resulting solution is cooled to a temperature of 0° to 5° C. or so, and seed crystals of a mirtazapine hydrate may be added to the solution in order to obtain a uniform crystal. The amount of the seed crystals is not limited to specified ones, and the amount can be 0.05 to 1 part by weight or so, based on 100 parts by weight of the crude mirtazapine.

In the procedures of dissolving and precipitating mirtazapine, it is preferable that the procedures are carried out in an inert gas atmosphere such as nitrogen, from the viewpoint of preventing coloration.

After the resulting crystals of a mirtazapine hydrate are collected by filtration, the crystals may be washed with, for instance, a water-soluble organic solvent such as methanol or ethanol, water, or a mixed solvent of the water-soluble organic solvent and water, and thereafter dried, as occasion demands. Thus, the crystals of a mirtazapine hydrate are obtained. The average particle diameter of the resulting crystals of a mirtazapine hydrate is usually 60 to 150 μm. The crystals may be pulverized with a pulverizer such as a hammer-mill as occasion demands.

Next, the process for preparing anhydrous mirtazapine crystals from the above-mentioned crystals of a mirtazapine hydrate will be explained.

The low-hygroscopic anhydrous mirtazapine crystals can be readily prepared by drying the crystals of a mirtazapine hydrate, which are obtained by crystallizing from a water-containing solvent as mentioned above. The anhydrous mirtazapine crystals have characteristic diffraction peaks in the X-ray diffraction pattern, when angles of diffraction (2θ) are 9.14, 9.38, 14.16, 18.46, 18.56 and 20.56.

Before drying the crystals of a mirtazapine hydrate, it is preferable to pulverize the crystals of a mirtazapine hydrate in order to efficiently dry the crystals. This pulverization is carried out after filtering the resulting crystals of a mirtazapine hydrate. It is preferable to predry the crystals of a mirtazapine hydrate in order to efficiently pulverize the crystals of a mirtazapine hydrate. The predrying can be carried out by heating the crystals of a mirtazapine hydrate to a temperature of 40° to 80° C. for 1 to 6 hours.

The pulverization can be carried out by using, for instance, a pulverizer such as a hammer-mill, a cutter mill or an atomizer. It is desired that the pulverization is carried out so that the average particle diameter of the crystals of a mirtazapine hydrate after the pulverization can be 10 to 70 μm or so, preferably 20 to 60 μm or so. The average particle diameter can be determined by using an apparatus commercially available from Shimadzu Corporation under the trade name of SALD1100, water as a medium, and Triton X-100 (trade name, commercially available from Rohm and Haas Co.) as a dispersing agent.

It is preferable that the drying is carried out under heating. In this case, it is desired that the heating temperature is 70° to 110° C., preferably 85° to 110° C., more preferably 90° to 105° C., from the viewpoint of shortening the drying time and the viewpoint of avoiding alteration of the mirtazapine hydrate.

The drying time can be furthermore shortened if the drying is carried out under reduced pressure. It is desired that the reduced pressure is 1.33 to 13300 Pa, preferably 10 to 6650 Pa, more preferably 100 to 1995 Pa, from the viewpoint of drying in a short period of time without using a powerful vacuum pump.

It is desired that the drying of the crystals of a mirtazapine hydrate is carried out until the water content of the resulting anhydrous mirtazapine crystals becomes not more than 0.5% by weight, preferably not more than 0.3% by weight, from the viewpoint of imparting excellent low hygroscopic properties to the resulting anhydrous mirtazapine crystals.

The mirtazapine crystals thus obtained exhibit remarkably excellent properties such that the hygroscopic degree is not more than 0.6% by weight even though the mirtazapine crystals are stored in the air having a relative humidity of 75% at 25° C. under atmospheric pressure for 500 hours.

As explained above, according to the process of the present invention, the low-hygroscopic anhydrous mirtazapine crystals can be easily prepared from the crystals of a mirtazapine hydrate as a starting material on an industrial scale.

EXAMPLES

Next, the present invention will be described more specifically on the basis of the examples, without intending to limit the present invention thereto.

Preparation Example

[Preparation of Crude Mirtazapine]

A 300 mL flask was charged with 144 g of concentrated sulfuric acid, and thereafter 40 g of 2-(4-methyl-2-phenylpiperazin-1-yl)pyridine-3-methanol was added to the flask, and the mixture was stirred at 30° to 40° C. for 8 hours.

The resulting reaction mixture was added in a thin stream to a 1 L flask charged with 258.8 g of water, and thereafter the inside of the flask was washed with 28.8 g of water. Next, pH of this reaction mixture was adjusted to about 1.8 with a 25% aqueous sodium hydroxide. The mixture was decolorized with 1.9 g of decolorizing carbon, and filtered and washed with 38 g of water.

Next, 60 mL of toluene was added to this solution after washing, and thereafter a 25% aqueous sodium hydroxide of about 50° C. was added to this solution to adjust its pH to 8.3. Thereafter, this solution was allowed to separate into two layers of aqueous layer and organic layer at 75° to 80° C. Forty-one grams of heptane was added in a thin stream to the organic layer at 55° to 60° C., and thereafter the mixture was cooled to 0° to 5° C. The mixture was stirred at the same temperature for one hour, and filtered.

The resulting crystals were washed with a cold mixed solvent (about 0° to about 5° C.) of 40 g of toluene and 31 g of heptane, and dried under reduced pressure at 60° C., to give 31.7 g of yellow crude mirtazapine. Its yield was 84.6%, and the purity as determined by high-performance liquid chromatography (hereinafter referred to as "HPLC purity") was 97.5%.

Example 1

Seventy-six grams of the crude mirtazapine (HPLC purity: 98.4%) was dissolved in 186 g of ethanol at 60° C., and 228 g of water and 760 mg of decolorizing carbon were added thereto. This solution was kept at 70° to 75° C. for 30 minutes. The resulting mixture was filtered, and the decolorizing carbon was washed with 6.2 g of ethanol. Thereafter, the resulting filtrate and washing liquid were cooled to 20° to 30° C.

Next, 714 g of water was added in a thin stream to this solution over 30 minutes, and the mixture was cooled to 0° to 5° C. for one hour. The crystals were filtered, and washed with a cold mixed solvent (about 0° to about 5° C.) of 15 g of ethanol and 80 g of water. Thereafter, the crystals were dried at 70° C., to give 77.05 g of crystals of mirtazapine hydrate. The physical properties of the resulting mirtazapine hydrate were as follows.

(1) Water content: 2.3% by weight
(2) HPLC purity: 99.6%
(3) Melting point: 121° to 123° C.
(4) Infrared absorption spectrum: shown in FIG. 1

Example 2

Seventy-one grams of the mirtazapine hydrate obtained in Example 1 was dissolved in 356 g of tert-butyl methyl ether at 50° C., and water and tert-butyl methyl ether were subjected to azeotropic dehydration at a temperature of 55° C. under atmospheric pressure, to distill off 255.3 g of tert-butyl methyl ether.

Next, this solution was cooled to 0° to 5° C., and the solution was aged for 30 minutes and filtered. The resulting crystals were washed with 52 g of cold tert-butyl methyl ether (about 0° to 5° C.), and dried, to give 52 g of white mirtazapine. HPLC Purity of this mirtazapine was 99.9%.

Example 3

Five grams of the mirtazapine hydrate obtained in Example 1 was predried under reduced pressure at 55° C. for 2 hours. The water content was 2.6% by weight.

Next, this predried mirtazapine hydrate was pulverized with a mortar, to give a powder having an average particle diameter [as determined by a measuring device commercially available from Shimadzu Corporation under the trade name of "SALD1100", medium: water, dispersing agent: Triton X-100 (trade name, commercially available from Rohm & Haas Co.), hereinafter referred to the same] of 20.97 μm.

This powder was dried under reduced pressure of 1333 Pa at 90° C. for 6 hours. As a result, the water content was 0.4% by weight. The average particle diameter of the powder after drying was determined. As a result, the average particle diameter was 41.2 μm.

Example 4

Five grams of the mirtazapine hydrate obtained in Example 1 was predried under reduced pressure at 55° C. for 2 hours. The water content was 2.8% by weight.

Next, this predried mirtazapine hydrate was pulverized with a mortar, to give a powder having an average particle diameter of 52.87 μm.

This powder was dried under reduced pressure of 1333 Pa at 90° C. for 10 hours. As a result, the water content was 0.25% by weight. The average particle diameter of the powder after drying was determined. As a result, the average particle diameter was 110.4 μm.

Example 5

Five grams of the mirtazapine hydrate obtained in Example 1 was predried under reduced pressure at 55° C. for 2 hours. The water content was 2.7% by weight.

Next, this predried mirtazapine hydrate was pulverized with a mortar, to give a powder having an average particle diameter of 47.7 μm.

This powder was dried under reduced pressure of 1333 Pa at 90° C. for 4 hours. As a result, the water content was 0.4% by weight. Moreover, the powder was dried for additional 3 hours. As a result, the water content was 0.27% by weight. The average particle diameter of the powder after drying was determined. As a result, the average particle diameter was 110.4 μm.

Comparative Example 1

Ten grams of the crude mirtazapine (HPLC purity: 98.4%) was dissolved in 13 g of toluene with heating at 75° C. The mixture was decolorized with 500 mg of decolorizing carbon, and filtered, and the filtrate was then cooled to 0° to 5° C. to allow precipitation. Thereafter, the mixture was filtered to collect crystals, and dried, to give 8.1 g of mirtazapine. Its hue was pale yellow, and contained insoluble matters which did not dissolve in methanol. HPLC Purity of this mirtazapine was 98.8%.

Comparative Example 2

Ten grams of the crude mirtazapine (HPLC purity: 98.4%) was dissolved in 15 g of tert-butyl methyl ether at 55° C., and the mixture was decolonized with 500 mg of decolorizing carbon, and filtered. The filtrate was cooled to 0° to 5° C. to allow precipitation.

The resulting crystals were filtered and dried, to give 8.6 g of mirtazapine. Its hue of the resulting mirtazapine was pale yellow, and contained insoluble matters which did not dissolve in methanol. HPLC Purity of the mirtazapine was 98.2%.

Production Example 1

The amount 1396.8 g of 1-(3-hydroxymethylpyridin-2-yl)-2-phenyl-4-methylpiperazine, prepared in accordance with a process disclosed in U.S. Pat. No. 4,062,848, was added in divided portions to a reaction vessel charged with 5027.9 g of purified concentrated sulfuric acid at 0° to 30° C. in nitrogen atmosphere with stirring. After the addition, the temperature inside the reaction vessel was kept at 30° to 40° C. for 8 hours.

Next, the resulting product was analyzed by high-performance liquid chromatography (hereinafter referred to as "HPLC"). As a result, the peak area of mirtazapine was 98.1% in the reaction solution.

To this reaction solution was added in a thin stream 8660 g of water at 0° to 5° C., and 1397 g of water was further added. Thereafter, a solution prepared by dissolving 3143 g of sodium hydroxide in 9428 g of water was added in a thin stream to this reaction solution at a temperature of not more than 30° C., and its pH was adjusted to 1 to 2. Next, 67 g of decolorizing carbon was added to the reaction solution at 20° to 30° C. to allow decoloration. The mixture was filtered, and the decolorizing carbon was washed with 1330 g of water. To the filtrate was added 2095 g of toluene to wash the filtrate. Thereafter, the toluene layer was separated away. To the aqueous layer was added 2095 g of toluene, and thereafter a solution prepared by dissolving 936 g of sodium hydroxide in 2810 g of water was added in a thin stream thereto at a temperature of not more than 50° C., and its pH was adjusted to not less than 8. Thereafter, the mixture was allowed to separate into two layers at 75° to 80° C., and the organic layer was collected.

Next, 2095 mL of heptane was added in a thin stream to this organic layer at 50° to 60° C. to allow precipitation of crystals. The mixture was cooled to 0° to 5° C., and thereafter aged for one hour. The mixture was filtered, and thereafter the crystals were washed with liquid prepared by mixing 1600 mL of toluene and 1600 mL of heptane, and cooling the mixture to 0° to 5° C., to give 1111.8 g of crude mirtazapine [absorbance at a wavelength of 600 nm: 2.4154, transmittance at a wavelength of 400 nm: 0.01%, b value of colorimeter: 22.0].

The yield of the resulting crude mirtazapine was 85%, and the HPLC purity was 99.0%.

Example 6

In 360 mL of methanol was dissolved 120 g of the crude mirtazapine obtained in Production Example 1, and 1.2 g of decolorizing carbon was added thereto to allow decoloration. The mixture was filtered, and the decolorizing carbon was then washed with 12 mL of methanol. Thereafter, 1116 mL of ion-exchanged water was added in a thin stream at 20° to 30° C. with stirring, and the mixture was aged for one hour.

Next, the solution was cooled to 0° to 5° C. for one hour, and the solution was filtered. Crystals were washed with liquid prepared by mixing 43.2 mL of methanol with 129.6 mL of ion-exchanged water of which liquid temperature was 0° to 5° C. The crystals were dried at 60° C., to give 121.25 g of crystals of mirtazapine hemihydrate (yield: 97.7%).

Example 7

The crystals of mirtazapine hemihydrate obtained in Example 6 were dried at 90° to 95° C. under reduced pressure of 1330 to 1862 Pa. The water content of the resulting anhydrous mirtazapine crystals was determined by Karl-Fischer method. As a result, the water content was 0.1% by weight. In addition, its melting point was 114° to 116° C.

Comparative Example 3

The crude mirtazapine obtained in Production Example 1 was recrystallized in accordance with a process disclosed in U.S. Pat. No. 4,062,848. Specifically, 20 g of the crude mirtazapine obtained in Production Example 1 was dissolved in 140 mL of tert-butyl methyl ether with heating, and 0.2 g of decolorizing carbon and 0.2 g of celite were added to the resulting solution to allow decoloration, and the mixture was filtered. The filtrate was concentrated until the amount of the solution attained to 41.2 g, and 5.4 g of tert-butyl methyl ether was added to the concentrate. The mixture was cooled to 3° C. to allow crystallization. Thereafter, the mixture was filtered, and the crystals were dried at 50° C., to give 16.5 g of mirtazapine crystals.

Next, 10 g of the crystals were dissolved in 200 mL of petroleum ether (boiling point: 40° to 60° C.) with heating. The resulting solution was cooled to 0° to 5° C., to give 4 g of mirtazapine crystals.

The resulting mirtazapine crystals were dried at 90° to 95° C. under reduced pressure of 1330 to 1995 Pa. The water content was determined by Karl-Fischer method. As a result, the water content was 0.1% by weight.

Figure 2:
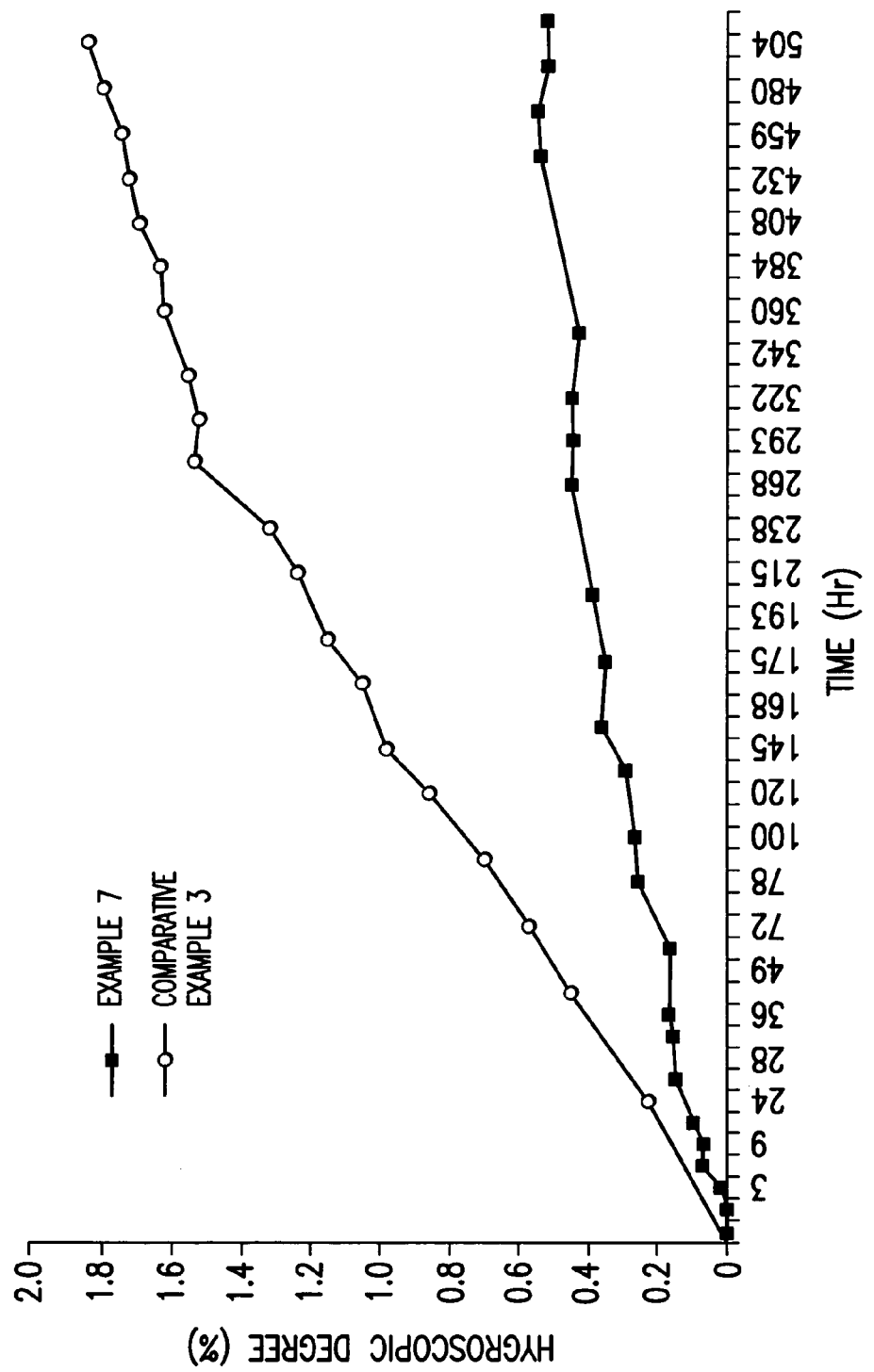
FIG. 2 is a graph showing the hygroscopic degree of the anhydrous mirtazapine crystals obtained in Example 7 of the present invention and Comparative Example 3 with the passage of time.

Next, the mirtazapine crystals obtained in Example 7 and Comparative Example 3 were placed on a petri dish, and the petri dish was placed in a constant temperature and humidity of 75% relative humidity and a chamber temperature of 25° C., and the change in the hygroscopic degree of the crystals was evaluated. The results are shown in FIG. 2. Incidentally, the hygroscopic degree is calculated by the following equation:

[Hygroscopic Degree (% by weight)]=[(Weight (g) of Crystals After Treatment)−(Weight (g) of Crystals Before Treatment)]÷[Weight (g) of Crystals Before Treatment]×100

As is clear from the results shown in FIG. 2, it can be seen that the anhydrous mirtazapine crystals obtained in Example 7 have a very low hygroscopic degree after 500 hours passed, so that they are remarkably excellent in low hygroscopic properties, as compared with that of the mirtazapine crystals obtained in Comparative Example 3.

Example 8

In 4728 g of methanol was dissolved 1195.46 g of a crude mirtazapine (HPLC purity: 99.0%) at 0° to 5° C., and 12 g of decolorizing carbon was added thereto, and the mixture was stirred at 5° C. for 15 minutes. This solution was filtered at 0° to 5° C. Thereafter, 4065 g of ion-exchanged water was introduced into the filtrate, and 100 mg of seed crystals were added thereto. Thereto was added in a thin stream 9707 g of ion-exchanged water at 0° to 10° C. to allow crystallization. The mixture was stirred at 0° to 5° C. for 1 hour, and crystals were filtered. The crystals were washed with a mixed solution (liquid temperature: 0° to 5° C.) of 340 g of methanol and 1291 g of ion-exchanged water. The crystals were dried under reduced pressure (4 to 5.3 kPa) at 50° to 60° C. so that the water content was attained to not more than 3.5% by weight. The crystals were pulverized with a pulverizer (hammer-mill), to give crystals of a mirtazapine hydrate having an average particle diameter of 20 μm.

Figure 3:
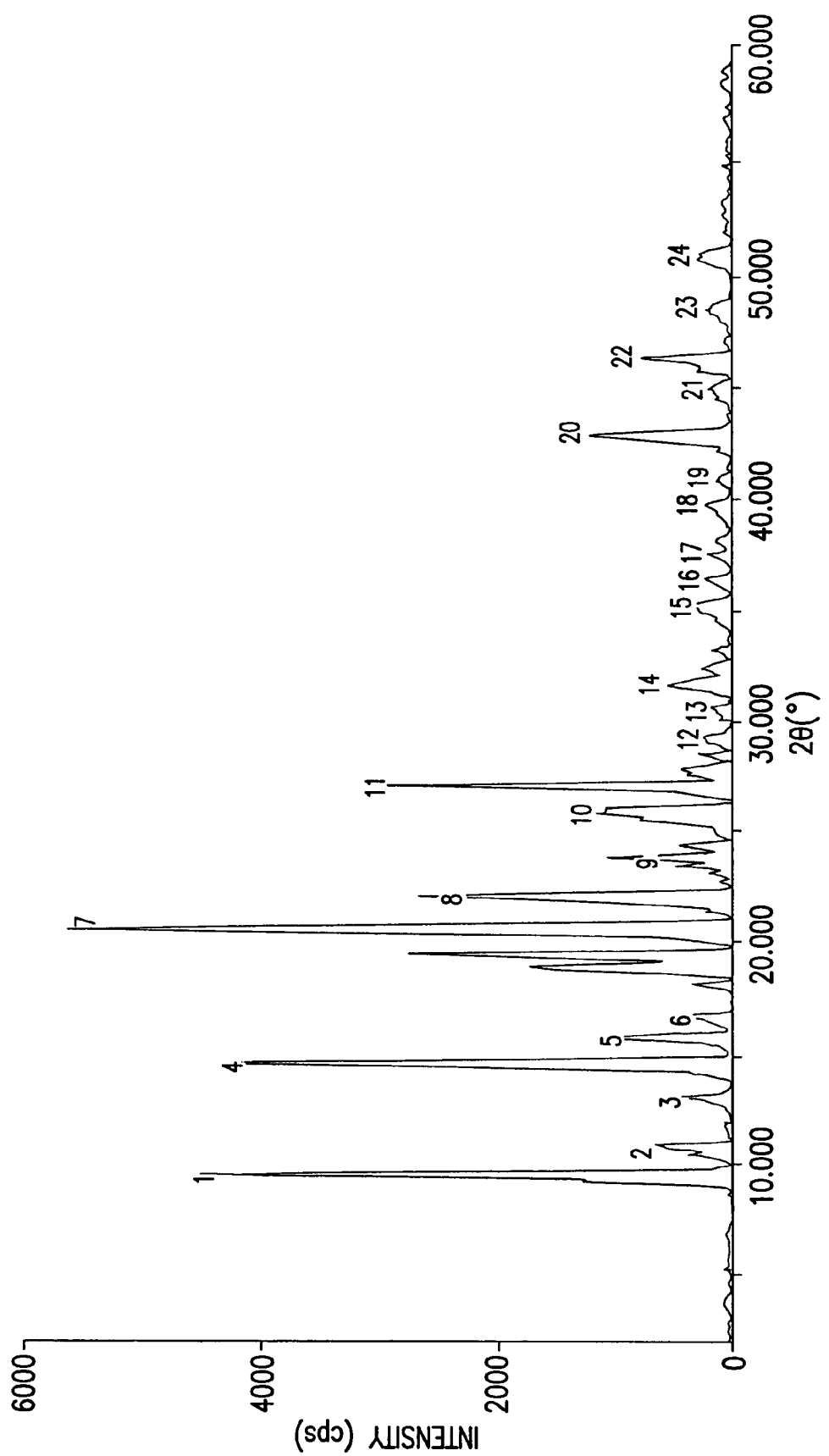
FIG. 3 is an X-ray diffraction pattern of the crystals of mirtazapine hydrate obtained in Example 8 of the present invention.

The X-ray diffraction of the crystals of a mirtazapine hydrate before pulverization was examined. The results are shown in FIG. 3. Determination conditions for the X-ray diffraction are shown below.

[Determination Conditions for the X-Ray Diffraction]
1) Determination device: commercially available from Rigaku Denki K.K., under the trade name of A7RV
2) Irradiated X-ray: CuKα rays
3) Accelerating voltage: 30 kV
4) Accelerating current: 15 mA Crystal parameters were determined on the basis of the results for X-ray diffraction. The results are as follows.
1) Crystal system: monoclinic system
2) Bravais lattice: Primitive (simple)
3) Space group: ($P2_1/\alpha$)
4) Z value: 4
5) Lattice parameters
   a =9.006(1) Å
   b =17.309(2) Å
   c =9.801(1) Å
   β=106.07(1)°
   V =1468.1(4) Å$^3$ The values obtained on the basis of the above results were precisely determined by least square method to calculate atomic coordinates, isotropic temperature factors (Beq) and occupying ratios (occ), anisotropic temperature factors, interatomic (bond) distances, bond angles, and angles of torsion.

The atomic coordinates, the isotropic temperature factors and the occupying ratios are shown in Table 1, the anisotropic temperature factors in Table 2, the interatomic (bond) distances in Table 3, and the interatomic bond angles in Table 4, and the angles of torsion in Table 5.

TABLE 1

| Atom | x | y | z | Beq | occ |
| --- | --- | --- | --- | --- | --- |
| O(1) | 0.0169(7) | −0.0493(4) | −0.0037(8) | 11.0(2) | 0.5000 |
| N(1) | 0.1821(3) | 0.0888(1) | 0.6597(2) | 4.48(5) | 1.0000 |
| N(2) | 0.2627(3) | 0.0830(1) | 0.4534(2) | 3.99(5) | 1.0000 |
| N(3) | 0.2717(3) | −0.0037(1) | 0.2097(2) | 5.13(6) | 1.0000 |
| C(1) | 0.2607(3) | 0.1216(1) | 0.5778(2) | 3.62(5) | 1.0000 |
| C(2) | 0.1886(4) | 0.1227(2) | 0.7839(3) | 5.23(7) | 1.0000 |
| C(3) | 0.2711(4) | 0.1893(2) | 0.8307(3) | 5.27(7) | 1.0000 |
| C(4) | 0.3545(3) | 0.2211(2) | 0.7466(2) | 4.55(6) | 1.0000 |
| C(5) | 0.3530(3) | 0.1877(1) | 0.6187(3) | 3.69(5) | 1.0000 |
| C(6) | 0.4462(3) | 0.2180(1) | 0.5253(3) | 3.79(5) | 1.0000 |
| C(7) | 0.3407(3) | 0.2520(1) | 0.3915(2) | 3.39(5) | 1.0000 |

TABLE 1-continued

| Atom | x | y | z | Beq | occ |
|---|---|---|---|---|---|
| C(8) | 0.3471(3) | 0.3302(1) | 0.3632(3) | 4.03(5) | 1.0000 |
| C(9) | 0.2487(3) | 0.3628(1) | 0.2438(3) | 4.70(6) | 1.0000 |
| C(10) | 0.1400(3) | 0.3174(2) | 0.1527(3) | 4.66(6) | 1.0000 |
| C(11) | 0.1297(3) | 0.2401(2) | 0.1800(3) | 4.05(5) | 1.0000 |
| C(12) | 0.2307(3) | 0.2057(1) | 0.2992(2) | 3.40(5) | 1.0000 |
| C(13) | 0.2177(3) | 0.1193(1) | 0.3117(2) | 3.54(5) | 1.0000 |
| C(14) | 0.3099(3) | 0.0784(2) | 0.2233(3) | 4.38(6) | 1.0000 |
| C(15) | 0.2984(4) | −0.0392(2) | 0.3476(3) | 5.35(7) | 1.0000 |
| C(16) | 0.2173(4) | 0.0017(2) | 0.4410(3) | 5.18(7) | 1.0000 |
| C(17) | 0.3634(6) | −0.0424(2) | 0.1267(5) | 8.6(1) | 1.0000 |
| H(1) | 0.1332 | 0.0995 | 0.8425 | 6.2218 | 1.0000 |
| H(2) | 0.2681 | 0.2126 | 0.9175 | 6.1018 | 1.0000 |
| H(3) | 0.4157 | 0.2659 | 0.7783 | 5.2451 | 1.0000 |
| H(4) | 0.5126 | 0.2572 | 0.5753 | 4.4192 | 1.0000 |
| H(5) | 0.5031 | 0.1773 | 0.5017 | 4.4192 | 1.0000 |
| H(6) | 0.4208 | 0.3626 | 0.4274 | 4.5866 | 1.0000 |
| H(7) | 0.2566 | 0.4163 | 0.2249 | 5.4196 | 1.0000 |
| H(8) | 0.0714 | 0.3397 | 0.0707 | 5.3280 | 1.0000 |
| H(9) | 0.0528 | 0.2093 | 0.1173 | 4.6048 | 1.0000 |
| H(10) | 0.1128 | 0.1068 | 0.2702 | 3.9873 | 1.0000 |
| H(11) | 0.4170 | 0.0844 | 0.2674 | 4.9206 | 1.0000 |
| H(12) | 0.2851 | 0.1012 | 0.1309 | 4.9206 | 1.0000 |
| H(13) | 0.4053 | −0.4053 | 0.3936 | 6.1278 | 1.0000 |
| H(14) | 0.2600 | −0.2600 | 0.3349 | 6.1278 | 1.0000 |
| H(15) | 0.1086 | −0.1086 | 0.4024 | 6.1871 | 1.0000 |
| H(16) | 0.2452 | −0.2452 | 0.5337 | 6.1871 | 1.0000 |
| H(17) | 0.4643 | −0.4643 | 0.1723 | 9.7575 | 1.0000 |
| H(18) | 0.3348 | −0.3348 | 0.0348 | 9.7575 | 1.0000 |
| H(19) | 0.3277 | −0.3277 | 0.1182 | 9.7575 | 1.0000 |

TABLE 2

| Atom | $U_{11}$ | $U_{22}$ | $U_{33}$ | $U_{12}$ | $U_{13}$ | $U_{23}$ |
|---|---|---|---|---|---|---|
| O(1) | 0.100(4) | 0.145(6) | 0.141(6) | −0.013(4) | −0.017(4) | −0.030(5) |
| N(1) | 0.055(1) | 0.065(1) | 0.065(1) | −0.002(1) | 0.0159(10) | 0.012(1) |
| N(2) | 0.064(1) | 0.039(1) | 0.051(1) | −0.0061(9) | 0.0165(10) | 0.0042(8) |
| N(3) | 0.081(2) | 0.050(1) | 0.056(1) | 0.013(1) | 0.006(1) | −0.0108(10) |
| C(1) | 0.044(1) | 0.046(1) | 0.046(1) | 0.0027(10) | 0.010(1) | 0.0080(10) |
| C(2) | 0.064(2) | 0.089(2) | 0.048(1) | 0.009(2) | 0.020(1) | 0.017(1) |
| C(3) | 0.070(2) | 0.086(2) | 0.042(1) | 0.014(2) | 0.012(1) | 0.000(1) |
| C(4) | 0.057(2) | 0.061(2) | 0.049(1) | 0.004(1) | 0.004(1) | −0.006(1) |
| C(5) | 0.042(1) | 0.045(1) | 0.048(1) | 0.0050(10) | 0.0051(10) | 0.006(1) |
| C(6) | 0.041(1) | 0.045(1) | 0.055(1) | −0.0033(10) | 0.008(1) | 0.000(1) |
| C(7) | 0.041(1) | 0.042(1) | 0.048(1) | 0.0008(9) | 0.0173(10) | 0.0019(10) |
| C(8) | 0.055(1) | 0.043(1) | 0.059(1) | −0.003(1) | 0.021(1) | −0.001(1) |
| C(9) | 0.072(2) | 0.043(1) | 0.068(2) | 0.005(1) | 0.026(1) | 0.013(1) |
| C(10) | 0.065(2) | 0.058(2) | 0.054(1) | 0.010(1) | 0.016(1) | 0.014(1) |
| C(11) | 0.054(1) | 0.052(1) | 0.047(1) | 0.000(1) | 0.013(1) | 0.004(1) |
| C(12) | 0.044(1) | 0.044(1) | 0.044(1) | 0.0019(9) | 0.0166(10) | 0.0009(9) |
| C(13) | 0.043(1) | 0.043(1) | 0.046(1) | −0.0006(10) | 0.0096(10) | −0.0016(10) |
| C(14) | 0.060(2) | 0.055(2) | 0.051(1) | 0.009(1) | 0.015(1) | −0.001(1) |
| C(15) | 0.082(2) | 0.041(1) | 0.069(2) | 0.003(1) | 0.001(2) | −0.003(1) |
| C(16) | 0.084(2) | 0.041(1) | 0.069(2) | −0.011(1) | 0.018(2) | 0.004(1) |
| C(17) | 0.152(4) | 0.086(3) | 0.088(3) | 0.043(3) | 0.035(3) | −0.020(2) |

TABLE 3

Interatomic Distance

| Atom | Atom | Distance (Å) | Atom | Atom | Distance (Å) |
|---|---|---|---|---|---|
| O(1) | O(1) | 1.74(1) | N(1) | C(1) | 1.334(3) |
| N(1) | C(2) | 1.337(4) | N(2) | C(1) | 1.395(3) |
| N(2) | C(13) | 1.475(3) | N(2) | C(16) | 1.460(3) |
| N(3) | C(14) | 1.460(4) | N(3) | C(15) | 1.442(4) |
| N(3) | C(17) | 1.471(4) | C(1) | C(5) | 1.406(3) |
| C(2) | C(3) | 1.380(5) | C(3) | C(4) | 1.375(4) |
| C(4) | C(5) | 1.378(4) | C(5) | C(6) | 1.498(3) |
| C(6) | C(7) | 1.510(3) | C(7) | C(8) | 1.385(3) |
| C(7) | C(12) | 1.395(3) | C(8) | C(9) | 1.378(4) |
| C(9) | C(10) | 1.375(4) | C(10) | C(11) | 1.373(4) |
| C(11) | C(12) | 1.399(3) | C(12) | C(13) | 1.508(3) |
| C(13) | C(14) | 1.530(3) | C(15) | C(16) | 1.497(4) |

TABLE 4

Interatomic Bond Angle

| Atom | Atom | Atom | Angle(°) | Atom | Atom | Atom | Angle(°) |
|---|---|---|---|---|---|---|---|
| C(1) | N(1) | C(2) | 117.7(2) | C(1) | N(2) | C(13) | 123.5(2) |
| C(1) | N(2) | C(16) | 117.6(2) | C(13) | N(2) | C(16) | 109.5(2) |
| C(14) | N(3) | C(15) | 110.8(2) | C(14) | N(3) | C(17) | 109.8(3) |
| C(15) | N(3) | C(17) | 110.6(3) | N(1) | C(1) | N(2) | 117.4(2) |
| N(1) | C(1) | C(5) | 123.0(2) | N(2) | C(1) | C(5) | 119.3(2) |
| N(1) | C(2) | C(3) | 123.6(3) | C(2) | C(3) | C(4) | 117.9(3) |
| C(3) | C(4) | C(5) | 120.5(3) | C(1) | C(5) | C(4) | 117.2(2) |
| C(1) | C(5) | C(6) | 119.9(2) | C(4) | C(5) | C(6) | 122.9(2) |
| C(5) | C(6) | C(7) | 110.1(2) | C(6) | C(7) | C(8) | 120.2(2) |
| C(6) | C(7) | C(12) | 120.2(2) | C(8) | C(7) | C(12) | 119.5(2) |
| C(7) | C(8) | C(9) | 121.2(2) | C(8) | C(9) | C(10) | 119.5(2) |
| C(9) | C(10) | C(11) | 120.3(2) | C(10) | C(11) | C(12) | 120.9(2) |
| C(7) | C(12) | C(11) | 118.6(2) | C(7) | C(12) | C(13) | 125.1(2) |
| C(11) | C(12) | C(13) | 116.3(2) | N(2) | C(13) | C(12) | 119.5(2) |
| N(2) | C(13) | C(14) | 106.6(2) | C(12) | C(13) | C(14) | 110.3(2) |
| N(3) | C(14) | C(13) | 110.6(2) | N(3) | C(15) | C(16) | 112.8(2) |
| N(2) | C(16) | C(15) | 109.5(2) | | | | |

TABLE 5

Interatomic Angle of Torsion

| Atom | Atom | Atom | Atom | Angle(°) | Atom | Atom | Atom | Atom | Angle(°) |
|---|---|---|---|---|---|---|---|---|---|
| N(1) | C(1) | N(2) | C(13) | 126.5(2) | N(1) | C(1) | N(2) | C(16) | -16.5(3) |
| N(1) | C(1) | C(5) | C(4) | -3.2(3) | N(1) | C(1) | C(5) | C(6) | 175.9(2) |
| N(1) | C(2) | C(3) | C(4) | -2.0(5) | N(2) | C(1) | N(1) | C(2) | 175.4(2) |
| N(2) | C(1) | C(5) | C(4) | -176.1(2) | N(2) | C(1) | C(5) | C(6) | 3.0(3) |
| N(2) | C(13) | C(12) | C(7) | 31.3(3) | N(2) | C(13) | C(12) | C(11) | -152.9(2) |
| N(2) | C(13) | C(14) | N(3) | 61.2(2) | N(2) | C(16) | C(15) | N(3) | -55.6(3) |
| N(3) | C(14) | C(13) | C(12) | -167.8(2) | C(1) | N(1) | C(2) | C(3) | 0.3(4) |
| C(1) | N(2) | C(13) | C(12) | 25.5(3) | C(1) | N(2) | C(13) | C(14) | 151.2(2) |
| C(1) | N(2) | C(16) | C(15) | -151.3(2) | C(1) | C(5) | C(4) | C(3) | 1.5(4) |
| C(1) | C(5) | C(6) | C(7) | 69.7(3) | C(2) | N(1) | C(1) | C(5) | 2.4(4) |
| C(2) | C(3) | C(4) | C(5) | 1.0(4) | C(3) | C(4) | C(5) | C(6) | -177.6(2) |
| C(4) | C(5) | C(6) | C(7) | -111.2(3) | C(5) | C(1) | N(2) | C(13) | -60.2(3) |
| C(5) | C(1) | N(2) | C(16) | 156.8(2) | C(5) | C(6) | C(7) | C(8) | 115.8(2) |
| C(5) | C(6) | C(7) | C(12) | -60.9(3) | C(6) | C(7) | C(8) | C(9) | -178.1(2) |
| C(6) | C(7) | C(12) | C(11) | 176.8(2) | C(6) | C(7) | C(12) | C(13) | -7.6(3) |
| C(7) | C(8) | C(9) | C(10) | 1.5(4) | C(7) | C(12) | C(11) | C(10) | 1.2(3) |
| C(7) | C(12) | C(13) | C(14) | -92.6(3) | C(8) | C(7) | C(12) | C(11) | 0.1(3) |
| C(8) | C(7) | C(12) | C(13) | 175.7(2) | C(8) | C(9) | C(10) | C(11) | -0.2(4) |
| C(9) | C(8) | C(7) | C(12) | -1.4(2) | C(9) | C(10) | C(11) | C(12) | -1.1(4) |
| C(10) | C(11) | C(12) | C(13) | -174.9(2) | C(11) | C(12) | C(13) | C(14) | 83.2(3) |
| C(12) | C(13) | N(2) | C(16) | 170.9(2) | C(13) | N(2) | C(16) | C(15) | 60.9(3) |
| C(13) | C(14) | N(3) | C(15) | -56.6(3) | C(13) | C(14) | N(3) | C(17) | -179.0(3) |
| C(14) | C(3) | C(15) | C(16) | 53.6(3) | C(14) | C(13) | N(2) | C(16) | -63.4(3) |
| C(16) | C(15) | N(3) | C(17) | 175.6(3) | | | | | |

Figure 4:
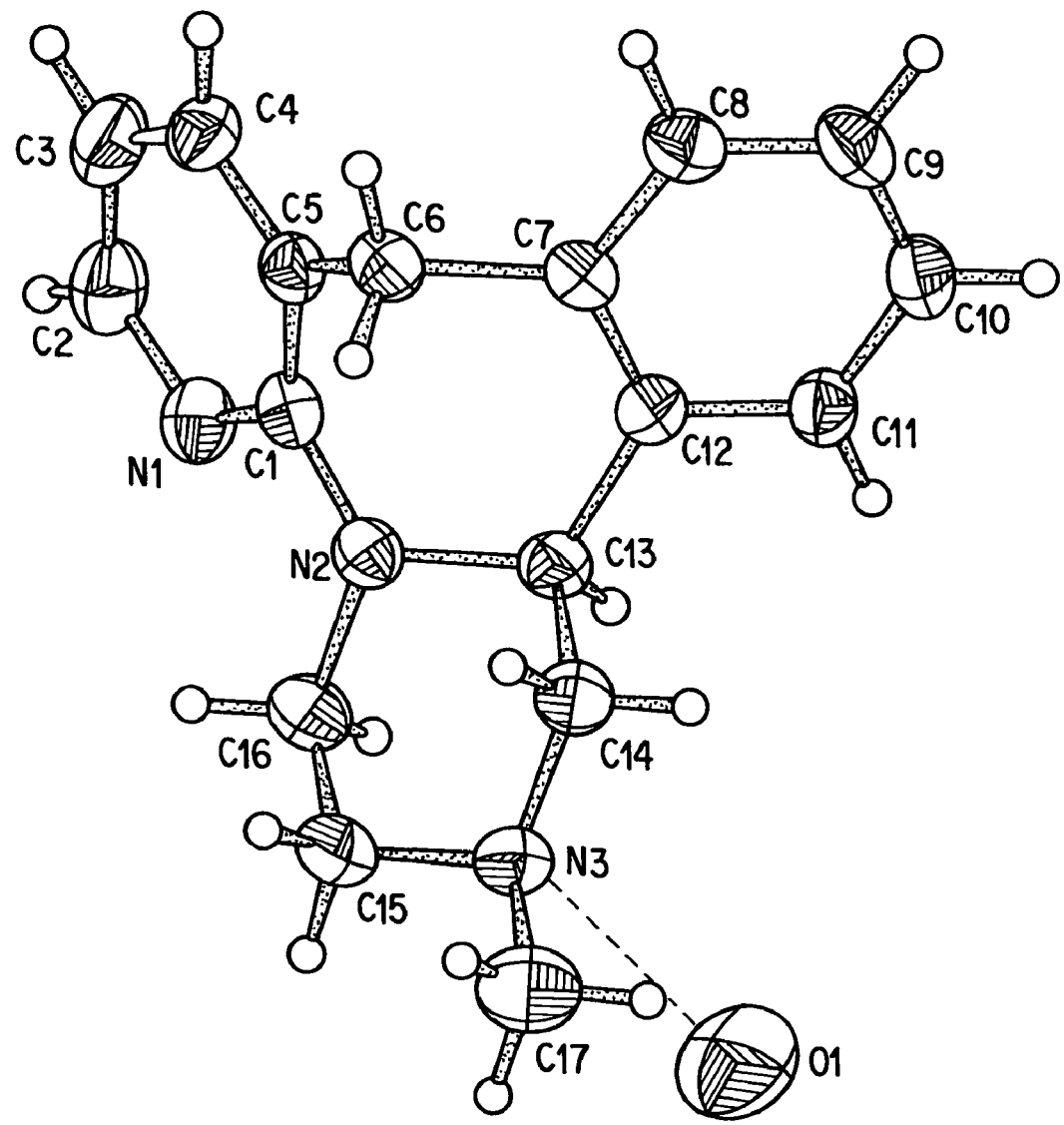
FIG. 4 is a molecular structure diagram of the crystals of mirtazapine hydrate obtained in Example 8 of the present invention.

On the bases of the above results, the molecular structure diagram of the mirtazapine hydrate obtained in Example 8 is shown in FIG. 4.

Figure 5:
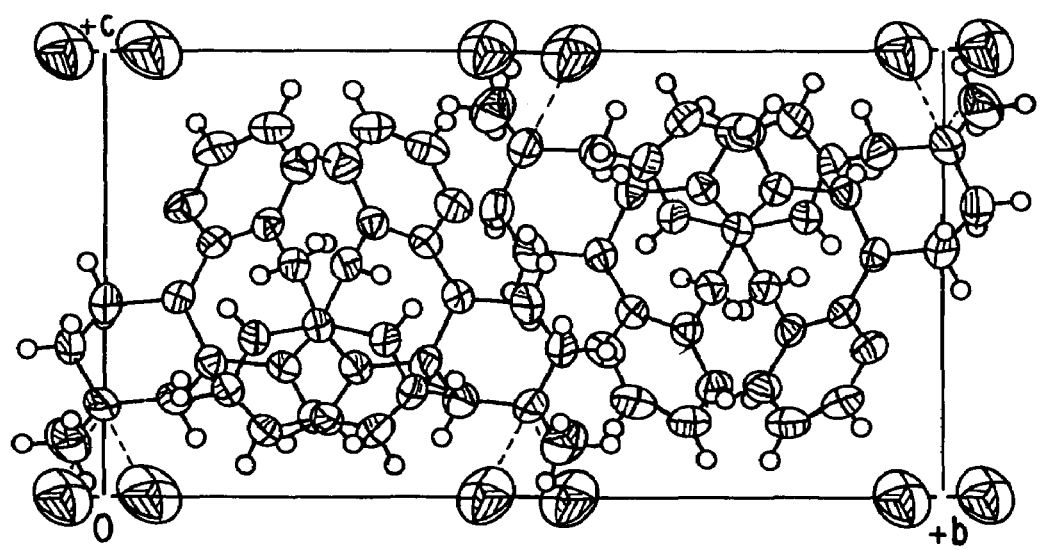
FIG. 5 is a crystal structure diagram viewed along the a axis of the crystals of mirtazapine hydrate obtained in Example 8 of the present invention.
Figure 6:
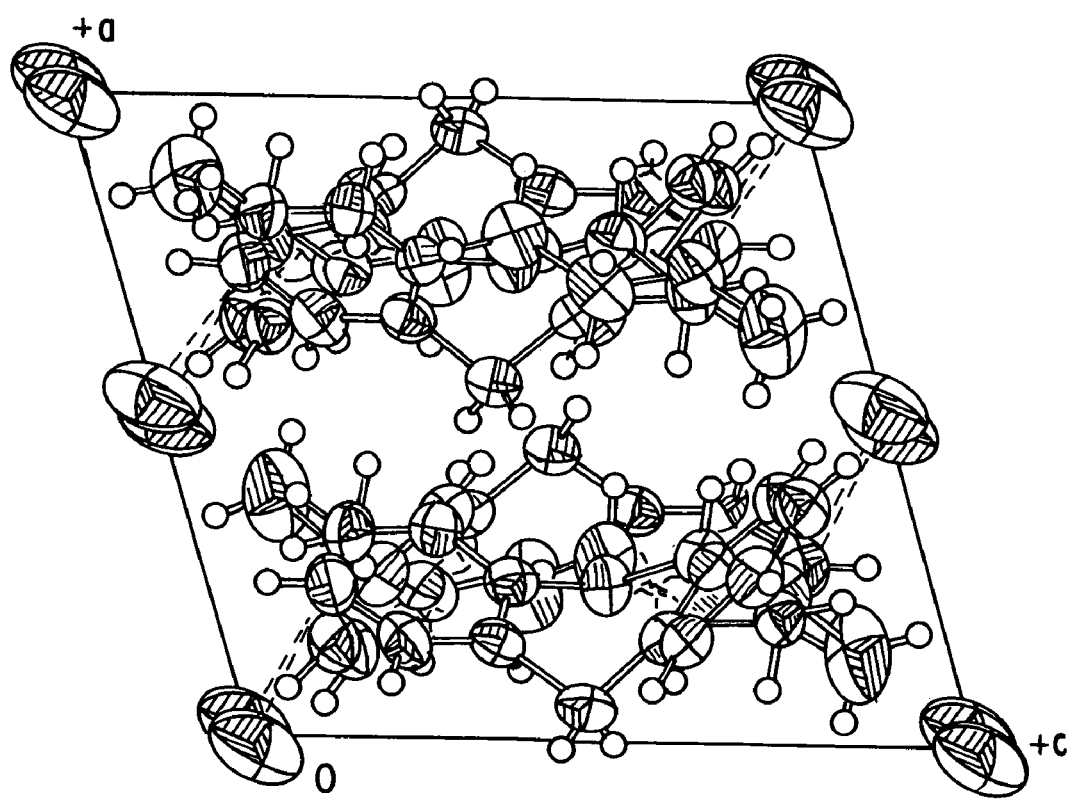
FIG. 6 is a crystal structure diagram viewed along the b axis of the crystals of mirtazapine hydrate obtained in Example 8 of the present invention.
Figure 7:
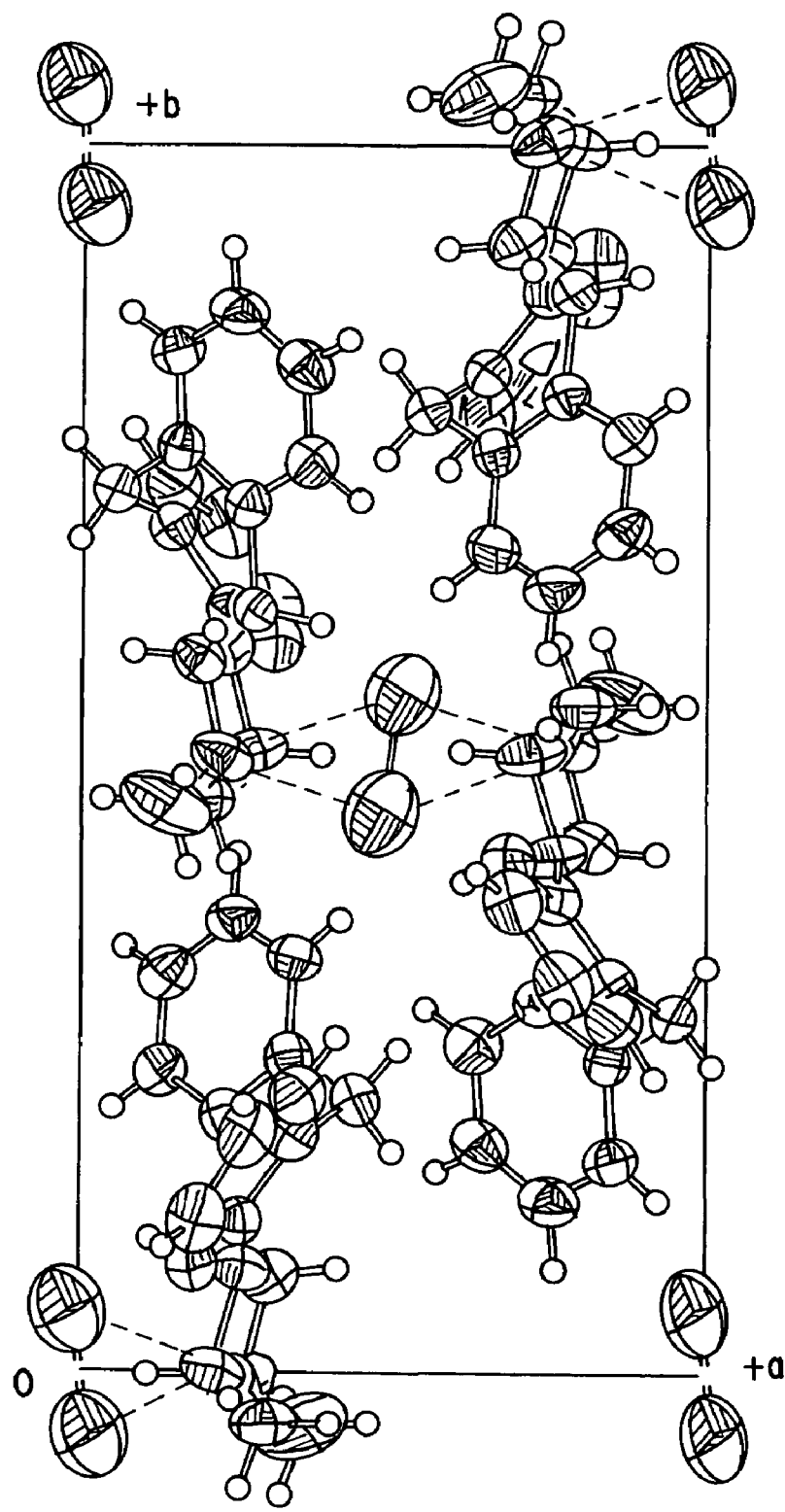
FIG. 7 is a crystal structure diagram viewed along the c axis of the crystals of mirtazapine hydrate obtained in Example 8 of the present invention.

In addition, the crystal structure diagrams viewed along the a axis, the b axis, and the c axis of the mirtazapine hydrate obtained in Example 8 are shown in FIGS. 5, 6 and 7, respectively.

In each figure, hydrogen atoms are geometrically calculated. Also, the positions of hydrogen atoms of the water molecules could not be determined from the electron density.

As is clear from the above results, it can be seen that the space group of the crystals of the mirtazapine hydrate obtained in Example 8 is $P2_1/\alpha$, has a center of symmetry, and exists in a racemic form.

The positions of oxygen atoms of the water molecules were estimated from the electron density distribution. As the electron density distribution was examined, it was found that there are two sites near the center of symmetry in which probability of existence was high. This distance is 1.75 Å. From the comparison of this distance with a van der Waals radius for oxygen atom of 1.4 Å, it can be thought that it would be less likely that two oxygen atoms exist at a distance of 1.75 Å. Therefore, it is estimated that oxygen atom of the water molecule does not simultaneously exist one each at these two sites, but randomly (probably with time) in any of two sites.

Therefore, assuming that oxygen exists at these two sites, precision was carried out by varying its occupying ratio as a parameter. As a result, the occupying ratio focused in the vicinity of 0.5.

It is thought from the above that one oxygen atom exists in a random state at these two sites. Finally, the occupying ratio was fixed at 0.5, and other parameters were precisely determined.

Since the occupying ratio of the water molecules was 0.5, the molar ratio of the mirtazapine molecules to the water molecules in the crystals was 2:1.

In addition, hydrogen bonding was formed between nitrogen atom of the mirtazapine molecule and oxygen atom of the water molecule in the crystal (in the figure, bonds shown by broken lines). Its bond distances were as follows. Incidentally, O(1)* is an atom in which O(1) was shifted by asymmetry operations.

N(1) . . . O(1):2.752(7)Å

N(1) . . . O(1)*:2.968(7)Å

Example 9

The mirtazapine hydrate obtained in Example 8 was dried in an atmosphere of 50° to 60° C. for 17 hours. As a result, the water content was 2.2%. Further, the mirtazapine hydrate was dried in an atmosphere of 85° to 95° C. for 23 hours. As a result, anhydrous mirtazapine crystals (average particle diameter: 118 μm) of which water content was 0.58% were obtained.

Figure 9:
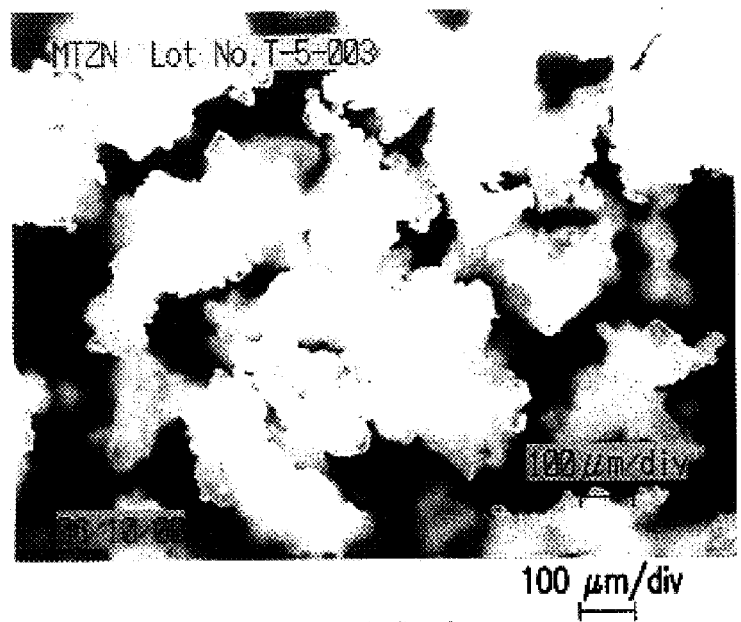
FIG. 9 is a microphotograph of particles obtained in Example 9 of the present invention, prepared by pulverizing the anhydrous mirtazapine crystals.

Next, the anhydrous mirtazapine crystals were pulverized, to give crystals having an average particle diameter of 59 μm. A microphotograph (magnification: ×200) of the resulting crystals is shown in FIG. 9.

Figure 10:
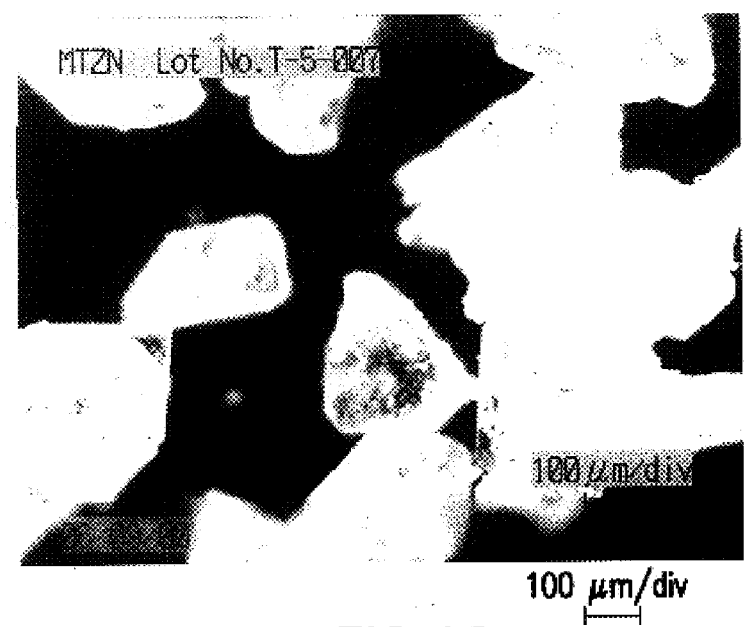
FIG. 10 is a microphotograph of particles obtained in Example 9 of the present invention, prepared by pulverizing the anhydrous mirtazapine crystals, and thereafter drying them.

Next, the resulting crystals were dried in an atmosphere of 85° to 95° C. for 6 hours. As a result, the water content was 0.14%. When the dried crystals were further dried in an atmosphere of 95° to 105° C. for 7 hours, the water content was 0.050%. The average particle diameter of the anhydrous mirtazapine crystals was 130 μm. A microphotograph (magnification: ×200) of the resulting crystals after drying is shown in FIG. 10.

As is clear from the above results, it can be seen that the disrupted anhydrous mirtazapine crystals were grown by drying.

Example 10

The crystals of the mirtazapine hydrate obtained in Example 8 were dried under reduced pressure of 600 to 1333

Figure 8:
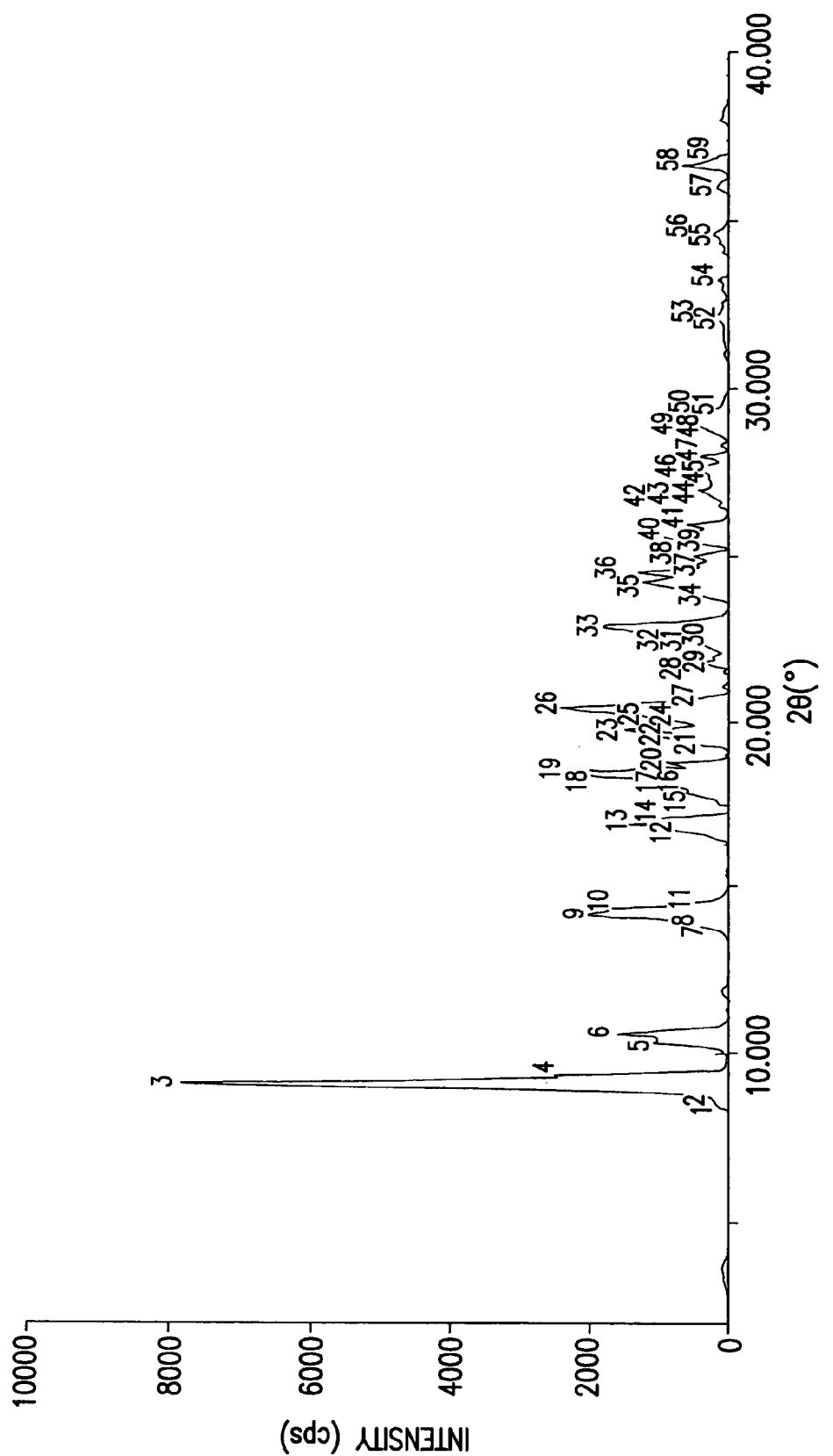
FIG. 8 is an X-ray diffraction pattern of the anhydrous mirtazapine crystals obtained in Example 10 of the present invention.

Pa at a temperature of 85° to 105° C. As a result, there were obtained 999.5 g of anhydrous mirtazapine crystals, of which water content after 6 hours passed from the initiation of drying was 0.46% by weight, and the water content after 10 hours passed therefrom was 0.3% by weight. The physical properties of the resulting anhydrous mirtazapine crystals are as follows.
(1) Water content: 0.3% by weight
(2) HPLC purity: 99.8%
(3) Powdered X-ray diffraction (the trade name: "Miniflex," commercially available from Rigaku Denki K.K., CuKα rays, 30 kV, 15 mV): Results are shown in FIG. 8.

Example 11

Eighty-four kilograms of the crude mirtazapine (HPLC purity: 98.8%) was dissolved in 332 kg of methanol at 2° to 4° C. under nitrogen atmosphere for 35 minutes with stirring. One kilogram of decolorizing carbon was added thereto, and the mixture was stirred at 2° to 4° C. for 30 minutes. The mixture was filtered at 0° to 2° C., and thereafter 285 kg of ion-exchanged water was introduced into the filtrate over 30 minutes, and 80 g of seed crystals were added thereto. To the resulting mixture was added in a thin stream 682 kg of ion-exchanged water at 5° to 7° C. to allow crystallization. The mixture was stirred at 1° to 5° C. for 65 minutes, and crystals were filtered. The crystals were washed with a mixed solution (liquid temperature: 0° to 5° C.) of 24 kg of methanol and 90.8 kg of ion-exchanged water. As a result, 93.3 kg of wet crystals were obtained. Its dry weight was 80.5 kg.

Eighty-seven kilograms of the wet crystals were added to 297.1 kg of methanol under nitrogen atmosphere, and the mixture was stirred at 2.8° C. Additional 24 kg of methanol was added thereto, and the mixture was stirred to dissolve the crystals. One kilogram of decolorizing carbon was added thereto, and the mixture was stirred at 3.3° C. for 15 minutes. The mixture was filtered at 3.4° C., and thereafter 255 kg of ion-exchanged water was added in a thin stream to the filtrate over 45 minutes, and 80 g of seed crystals were added to the resulting mixture. Thereto was added in a thin stream 666 kg of ion-exchanged water at 5° to 7.8° C. over 75 minutes, and the mixture was stirred at 2.6° to 5° C. for 40 minutes, and thereafter filtered. The resulting crystals were washed with a mixed solution (liquid temperature: 2.6° C.) of 21.6 kg of methanol and 81.2 kg of ion-exchanged water, to give 83.9 kg of wet crystals. The wet crystals were dried under reduced pressure of 266 to 533 Pa at 60° to 95° C. for 11 hours, to give 72.5 kg of a mirtazapine hydrate. Its yield was 89.5%.

Next, the resulting crystals were pulverized with an atomizer. There were further dried 54.3 kg of the pulverized crystals under reduced pressure of 133 to 400 Pa at 90° to 95° C. for 7 hours, to give 52.5 kg of anhydrous mirtazapine. The purity of the anhydrous mirtazapine crystals was 99.997%. The average particle diameter of the resulting crystals was 25.5 μm. The trapped density was 0.27 g/mL, and the bulk density was 0.51 g/mL. In addition, the absorbance was 0.0048 at a wavelength of 600 nm, the transmittance was 98.84% at a wavelength of 400 nm, and b value of the colorimeter was 2.42.

According to the process of the present invention, there is exhibited an effect that stable anhydrous mirtazapine crystals having almost no hygroscopic property can be prepared by a convenient industrial process.

In addition, since the anhydrous mirtazapine crystals of the present invention have excellent low hygroscopic property, they can be suitably used, for instance, as an antidepressant.

EQUIVALENT

Those skilled in the art will recognize, or be able to ascertain using simple routine experimentation, many equivalents to the specific embodiments of the invention described in the present specification. Such equivalents are intended to be encompassed in the scope of the present invention as recited in the following claims.

What is claimed is:

1. Low-hygroscopic anhydrous mirtazapine crystals having (i) a water content of not more than 0.5% by weight and (ii) a hygroscopic degree of not more than 0.6% by weight when the crystals are stored in the air having a relative humidity of 75% at 25° C. under atmospheric pressure for 500 hours.

2. The anhydrous mirtazapine crystals according to claim 1, wherein the crystals have characteristic diffraction peaks in the X-ray diffraction pattern, when angles of diffraction (2θ) are 9.14, 9.38, 14.16, 18.46, 18.56 and 20.56.

3. The anhydrous mirtazapine crystals according to claim 1, wherein the crystals are prepared by a process comprising a step of drying the pulverized crystals at a heating temperature of 70° C. to 110° C. under a reduced pressure of 1.33 to 1995 Pa until the water content of the resulting anhydrous mirtazapine crystals becomes not more than 0.5% by weight.

4. Low-hygroscopic anhydrous mirtazapine crystals of unlabeled mirtazapine having (i) a water content of not more than 0.5% by weight and (ii) a hygroscopic degree of not more than 0.6% by weight when the crystals are stored in the air having a relative humidity of 75% at 25° C. under atmospheric pressure for 500 hours.

5. Low-hygroscopic anhydrous mirtazapine crystals of unlabeled mirtazapine having (i) a water content of not more than 0.5% by weight and (ii) a hygroscopic degree of not more than 0.6% by weight when the crystals are stored in the air having a relative humidity of 75% at 25° C. under atmospheric pressure for 500 hours, wherein the melting point of the crystals is 114-116° C.

6. Low-hygroscopic anhydrous mirtazapine crystals of mirtazapine having (i) a water content of not more than 0.5% by weight and (ii) a hygroscopic degree of not more than 0.6% by weight when the crystals are stored in the air having a relative humidity of 75% at 25° C. under atmospheric pressure for 500 hours, wherein the melting point of the crystals is 114-116° C.

* * * * *